United States Patent [19]

Daneshtalab et al.

[11] Patent Number: 5,530,134
[45] Date of Patent: Jun. 25, 1996

[54] SYNTHESIS OF ANABASEINE, SALTS AND DERIVATIVES THEREOF

[75] Inventors: Mohsen Daneshtalab; Dai Nguyen; Inderjit Sidhu, all of Edmonton; Ronald G. Micetich, Sherwood Park, all of Canada

[73] Assignee: Synphar Laboratories Inc., Edmonton, Canada

[21] Appl. No.: 301,030

[22] Filed: Sep. 6, 1994

[51] Int. Cl.$^6$ .................. C07D 401/04; C07D 211/68
[52] U.S. Cl. ..................... 546/249; 546/257; 546/334
[58] Field of Search .................... 546/249, 257, 546/334

[56] References Cited

PUBLICATIONS

Tetrahedron Letters, vol. 24, No. 18, pp. 1937–1940, 1983 Synthesis of Tobacco Alkaloids Via Teritiary Azides, Alberici et al.
Synthetic Communications, 2(4), 197–200 (1972), Bradford P. Mundy and Brent R. Larsen, A New Approach To Pyrrolidine and Piperidine Alkaloids.
Spath, Mamoli, 69, 1082–1085, Chemical Ber. (1936).
The Journal of Organic Chemistry, vol. 44, No. 2, Jan. 19, 1979, Aberrant Biosynthesis of 5–Fluoroanabasine from 5–Fluoro[5,6–$^{14}$C,$^{13}$C$_2$]Nicotinic Acid, Established by Means of Carbon–13 Nuclear Magnetic Resonance, $^1$, Leete, Edward.

*Primary Examiner*—Zinna Northington Davis
*Attorney, Agent, or Firm*—Nikaido, Marmelstein, Murray & Oram

[57] ABSTRACT

A process for the synthesis of compounds of the formulas Ia and Ib below, wherein $R_1$, $R_2$, and $R_3$, which are the same or different, are each selected from hydrogen and $C_1$–$C_4$ alkyl, including the compound Anabaseine (Ia, wherein $R_1=R_2R_3=H$) (3,4,5,6-tetrahydro-2', 3'-bipyridine), the process comprising reacting sodium salt of δ-valerolactone with substituted ethyl nicotinate derivative to produce the Claisen product sodium 3-nicotinoyl-2-tetrahydropyranone enolate derivative, heating the sodium 3-nicotinoyl-2-tetrahydropyranone enolate derivative with concentrated HCl to produce 3-(5-chloro-1-pentanone-1-yl) pyridine derivative, dissolving the 3-(5-chloro-1-pentanone-1-yl) pyridine derivative in ethanol and then heating the 3-(5-chloro-1-pentanone-1-yl) pyridine derivative in ethanol with ethanolic ammonia solution in a sealed container to produce the compound Ia. Also, the process steps in the above process, and the products and intermediate products produced thereby.

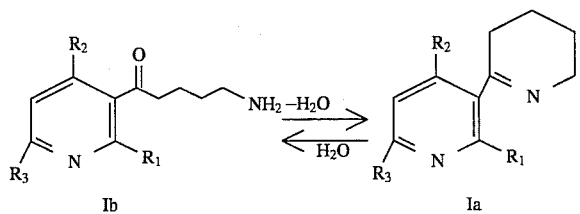

4 Claims, No Drawings

SYNTHESIS OF ANABASEINE, SALTS AND DERIVATIVES THEREOF

FIELD OF THE INVENTION

The present invention relates to a novel process for the preparation of Anabaseine and related compounds. Anabaseine is a naturally occurring neurotoxin, which has been recently further modified structurally to develop a class of nicotinic receptor binding agents for use in treating Alzheimer diseases.

BACKGROUND OF THE INVENTION

Synthesis of Anabaseine has been reported by Alberici et al (Tetrahedron Lett. 1983, 24, 1937-) by the addition of 3-pyridyl lithium to cyclopentanone followed by Schmidt reaction with hydrazoic acid; Mundy et al (Syn. Commun. 1972, 2, 197) by the rearrangement of 1-nicotinyl-2-piperidone induced by CaO; Spath et al (Chem. Ber. 1936, 69, 1082) through the benzoylation of 2-piperidone followed by reaction with nicotinamide and treatment with concentrated HCl; and Leete (J. Org. Chem 1979, 44, 165) by the Claisen reaction of 1-trimethylsilyl-2-piperidone with ethyl nicotinate using lithium diisopropyl amine (LDA) at −78° C. followed by the acid hydrolysis of the product. Due to the instability of Anabaseine, the base form, the most stable dihydrochloride salt which bears the open chain form of Ib (depicted below), has been reported in the above literature.

SUMMARY OF THE INVENTION

In accordance with the present invention, there is provided a new and convenient process comprising one-pot Claisen condensation of δ-valerolactone with ethyl nicotinate followed by hydrolysis, decarboxylation and chlorination to afford 3-(5-chloro-1-pentanone-1-yl)-pyridine (III). The invention also includes ammonolysis of III to produce Ia which forms the dihydrochloride salt Ib upon treatment with concentrated HCl and water.

DESCRIPTION OF THE PREFERRED EMBODIMENT

Numerous suitable specific sequences of process steps for carrying out the present invention will be apparent to those of skill in this art.

In accordance with a preferred embodiment according to the present invention, the sodium salt of δ-valerolactone (prepared by the reaction of sodium hydride with δ-valerolactone in tetrahydrofuran (THF)) is allowed to react with substituted ethyl nicotinate derivative to afford the Claisen product sodium 3-nicotinoyl-2-tetrahydropyranone enolate derivative (II). This reaction can be carried out at any suitable temperature, e.g., preferably 15°–35° C. Compound II is heated with concentrated HCl for one hour to afford 3-(5-chloro-1-pentanone-1-yl) pyridine derivative (III). This step can be conducted at any suitable temperature,. e.g., preferably about 110° C. After purification, e.g., by silica gel column chromatography or distillation, compound III is dissolved in ethanol and heated with ethanolic ammonia solution in a sealed tube to afford compound Ia. This step can be conducted at any suitable temperature and for any suitable duration, e.g., preferably about 115°–125° C. for 4–6 hours. Compound Ia is then dissolved in isopropanol and heated with 6N HCl to give compound Ib as dihydrochloride salt. This step can be conducted at any suitable temperature, e.g., preferably at about the reflux temperature (i.e., the boiling point for isopropanol).

The process according to the present invention has several advantages over the previously reported ones in the simplicity of the method since (1) all steps can be carried out at room temperature or reflux condition; (2) the process uses δ-valerolactone which is a cheap commercially available reagent; and (3) the process can be performed using an industrially viable ammonolysis procedure (see Scheme I, below). The compounds according to formula Ia given below are useful as nicotinic receptor binding agents for use in treating Alzheimer diseases and compounds according to formula Ib below are useful as a stable form which can be readily converted to the compounds of formula Ia. The compounds according to formula II and formula III below are useful as intermediates which can be converted into the compounds formula Ia.

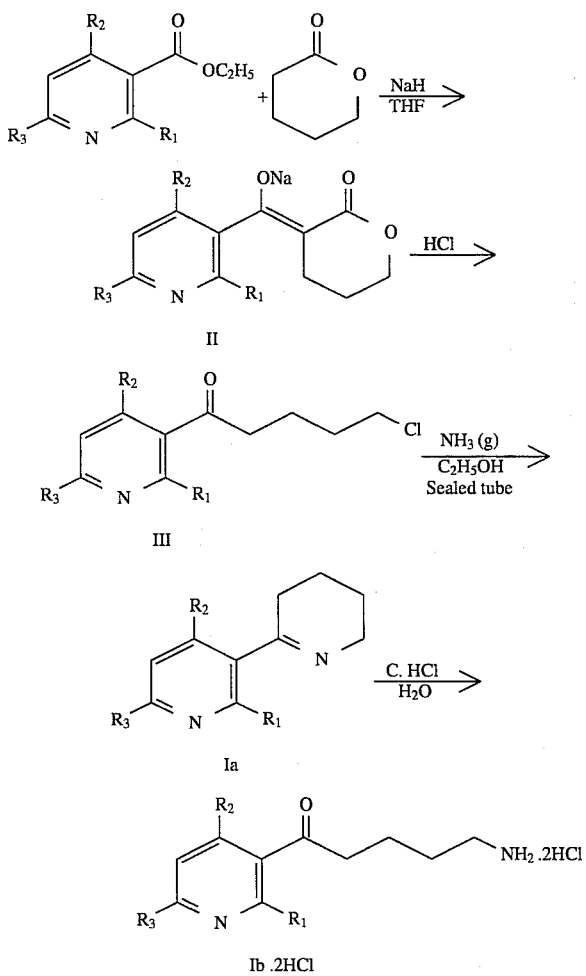

SCHEME I wherein $R_1$, $R_2$, and $R_3$, which are the same or different, are each selected from hydrogen and $C_1$–$C_6$ alkyl.

In accordance with a specific example of a preferred embodiment according to the present invention, the sodium salt of δ-valerolactone (prepared by the reaction of 0.050 moles of sodium hydride with 0.033 moles of δ-valerolactone in tetrahydrofuran (THF)) is allowed to react with 0.022 moles of substituted ethyl nicotinate derivative at 15°–35° C. to afford the Claisen product sodium 3-nicotinoyl-2-tetrahydropyranone enolate derivative (II). Compound II is heated at about 110° C. with concentrated HCl for one hour to afford 3-(5-chloro-1-pentanone-1-yl) pyridine derivative (III). After purification by silica gel column chromatography or distillation, compound III is dissolved in ethanol and heated with ethanolic ammonia solution in a sealed tube at 115°–125° C. for 4–6 hours to afford compound Ia, which is then dissolved in isopropanol and heated at the reflux temperature with 6N HCl to give compound Ib as dihydrochloride salt.

EXAMPLE 1

3-(5-chloro-1-pentanone-1-yl)pyridine

In a dry flask 3.1 mL (0.033 moles) of δ-valerolactone was dissolved in 200 mL of tetrahydrofuran under $N_2$ stream. The clear solution was cooled in an ice bath and 1.19 g (0.050 moles) of NaH was added to it. The gray suspension was stirred for 30 minutes at 0° C., then for 30 minutes at room temperature. The contents were cooled to 0° C. and a solution of 3.0 mL (0.022 moles) of ethyl nicotinate in 10 mL of tetrahydrofuran was dropped slowly. The dark gray suspension was slowly brought to room temperature and stirred for 14 hours. The solvent was removed under reduced pressure and the resulting solid was suspended in 200 mL of ether.

The solid [sodium 3-nicotinoyl-2-tetrahydropyranone enolate (II, wherein $R_1=R_2=R_3=H$)] was separated by filtration and the filtrate contained 670 mg of unreacted ethylnicotinate. Compound II was then transferred to a flask containing 30 g of crushed ice and to this dark brown solution, 100 mL of concentrated HCl was added. The contents were heated at 110° C., under $N_2$, for 1 hour and after cooling, poured onto 100 g of crushed ice. The dark brown solution was basified to pH≅8 with $Na_2CO_3$ (solid). The basified suspension was extracted with ethyl acetate (2×150 mL) and the combined organic layers, after drying over $Na_2SO_4$, were concentrated to a dark brown oil. This was chromatographed on a flash silica gel column (7:3 Hexane:Ethylacetate as eluent) to obtain 2.29, g of product III ($R_1=R_2=R_3=H$). The yield was found to be 66% for every mole of ethylnicotinate consumed. IR: 3000, 2880, 1690(C=O), 1583,1416 $cm^{-1}$; MS (FAB): $(M+H)^+$ 198; $^1H$. NMR ($CDCl_3$, 200 mHZ) :9.18(dd,2.0,1.0 Hz, H2'); 8.79(dd,4.9,1.5 Hz,H6'); 8.24(ddd, 8.3,2.0,1.5 Hz, H4') ; 7.43 (ddd,8.3,4.9,1.0 Hz,H5') ;3.60(t,6.1 Hz,H2α,β) ;3.05(t, 6.8 Hz,H560 ,β); 1.92 (m,H3α,β & H4α,β).

EXAMPLE 2

3-(5-Amino-1-pentanone-1-yl)pyridine dihydrochloride

In a flask, 60 mL of 95% ethanol was cooled in dry ice acetone bath and ammonia gas was bubbled through it until the final volume almost doubled. In a separate flask, 3-(5-chloro-1-pentanone-1-yl)pyridine (III) was mixed with 50 mL of 98% ethanol and transferred to a steel cylinder and cooled in dry ice acetone bath. The cylinder was kept under $N_2$ atmosphere to avoid condensation of moisture in the cylinder. The ammonical solution of ethanol was then transferred into the cylinder, capped and heated at 120 ° C. for 4 hrs. The cylinder was then cooled to room temperature and the pressure was released gently. The light brown solution was evaporated to a volume of 15 mL under reduced pressure. After adding 300 mL of dichloromethane, the insoluble greenish solid was removed by filtration. The filtrate was evaporated under reduced pressure to a dark brown oil (Anabaseine base). This was diluted with 200 mL of isopropanol and 2 mL of 6 N HCl was added with stirring and then dropwise addition of concentrated HCl was made until precipitates formed in the solution (5 mL of conc. HCl). The contents were further diluted with 100 mL of isopropanol and heated at about the reflux temperature until it began to reflux. Additional amounts of 6 N HCl and conc. HCl were added (2 mL+5 mL) until all the solid dissolved. The contents were then cooled slowly to room temperature at which time crystals began to appear in the solution. The colorless crystals were separated by filtration and the filtrate was concentrated to a volume of 100 mL to obtain a second crop of crystals. The first crop on drying weighed 2.341 g while the second crop weighed 1.870 to give a total of 4.211 g of product Ib ($R_1=R_2=R_3=H$). (Yield =67%. ). M.P.: 174–178 $O_c$ (decomposition);

ANALYSIS: Calculated for $C_{10}H_{16}Cl_2N_2O$: C,47.82; H, 6.42; Cl, 28.23; N,11.16. Found: C,48.20; H, 6.35; Cl, 28.86; N,10.95; $^1H$ NMR (DMSO-$d_6$, 200 mHZ): 9.23(d,2.4 Hz,H2'); 8.89(dd,4.9,1.5 Hz,H6'); 8.50(ddd, 7.9,2.4,1.5Hz, H4'); 7.97(b,$NH_2$); 7.75(dd,7.9,4.9 Hz,H5'); 3.17(t, 6.6 Hz,H2α,β); 2.82(m,H5α,β); 1.66(m,H3α,β & H4α,β).

What is claimed is:

1. A process for the synthesis of a compound according to formula Ia or a salt of said compound, the salt having the formula Ib:

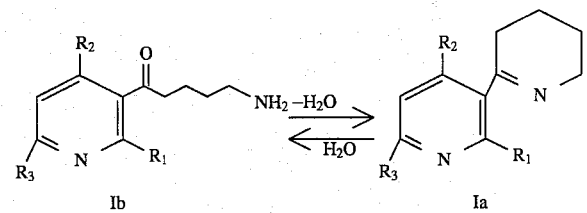

wherein $R_1$, $R_2$, and $R_3$, which are the same or different, are each selected from hydrogen and $C_1$–$C_6$ alkyl, comprising reacting sodium salt of δ-valerolactone with substituted ethyl nicotinate derivative to produce the Claisen product sodium 3-nicotinoyl-2-tetrahydropyranone enolate derivative, of the formula II;

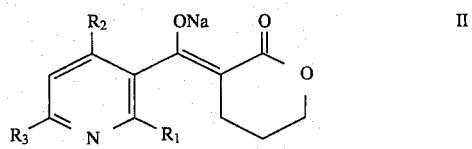

wherein $R_1$, $R_2$, and $R_3$ are the same as above;

heating said sodium 3-nicotinoyl-2-tetrahydropyranone enolate derivative with concentrated HCl to produce 3-(5-chloro-1-pentanone-1-yl) pyridine derivative, of the formula III;

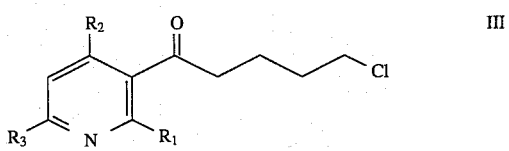

wherein $R_1$, $R_2$, and R3 are the same as above;

dissolving said 3-(5-chloro-1-pentanone-1-yl) pyridine derivative in ethanol and then heating said 3-(5-chloro-1-pentanone-1-yl) pyridine derivative in ethanol with ethanolic ammonia solution in a sealed container to produce the compound Ia.

2. A process as recited in claim 1, wherein said sodium salt of δ-valerolactone is prepared by reacting sodium hydride with δ-valerolactone in tetrahydrofuran.

3. A process as recited in claim 1, further comprising dissolving said compound Ia in isopropanol and then heating said compound Ia in isopropanol with 6N HCl to produce said salt Ib.

4. A process as recited in claim 1, wherein $R_1$, $R_2$, and $R_3$ are each hydrogen.

* * * * *